US005736320A

United States Patent [19]
Schlederer et al.

[11] Patent Number: 5,736,320
[45] Date of Patent: Apr. 7, 1998

[54] METHOD OF DETECTING SUBSTANCES BY CHEMILUMINESCENCE

[76] Inventors: Thomas Schlederer, 21 Dragonerweg, A-1220 Vienna; Peter Gerald Fritz, 76 D Hammerauerstrasse, A-6020 Salzburg, both of Austria

[21] Appl. No.: 522,530

[22] Filed: Sep. 5, 1995

Related U.S. Application Data

[63] Continuation of Ser. No. 96,818, Jul. 29, 1993, abandoned.

[30] Foreign Application Priority Data

May 12, 1993 [AT] Austria ............................ 936/93

[51] Int. Cl.$^6$ ..................... G01N 33/535; C12Q 1/70
[52] U.S. Cl. ................. 435/5; 435/7.1; 435/7.9; 435/14; 435/28; 435/974; 436/164; 436/172
[58] Field of Search ................... 435/5, 7.1, 7.9, 435/14, 28, 974; 436/127, 128, 164, 172, 800; 252/700

[56] References Cited

FOREIGN PATENT DOCUMENTS

| | | |
|---|---|---|
| 0408463 | 1/1991 | European Pat. Off. . |
| 280824 | 7/1990 | Germany . |
| 4225340 | 2/1994 | Germany . |
| 62-048398 | 3/1987 | Japan . |
| 1461877 | 1/1977 | United Kingdom . |
| 2233450 | 1/1991 | United Kingdom . |
| 2233451 | 1/1991 | United Kingdom . |
| 9108490 | 6/1991 | WIPO . |
| 00066 | 9/1994 | WIPO . |

OTHER PUBLICATIONS

Tsuji et al., in *Bioluminescence and Chemiluminescence: Instruments and Applications*, vol. 1 (1985), Ed. by Van Dyke, CRC: Boca Raton, Florida, Chapter 8, pp. 185–192 "Enzyme Immunoassay Monitored by Chemiluminescence Reaction Using the Bis(2,4,6-Trichlorophenyl)Oxalate Fluorescent Dye System".

Grayeski et al., Anal. Biochem., vol. 136, pp. 277–284 (1984) "Determination of Fluorophor–Labeled Compounds Based on Peroxyoxalate Chemiluminescence".

Hemmila, Clin. Chem. vol. 31, No. 3, pp. 359–370 (1985) "Fluoroimmunoassays and Immunofluorometric Assays".

Irena Bronstein, Ph.D. et al, "Chemiluminescent Compounds for Diagnostic Tests," *Research*, 28:36–39 (1990).

Anthony K. Campbell et al., "A Homogeneous Immunoassay For Cyclic Nucleotides Based on Chemiluminescence Energy Transfer," *Biochem. J.*, 216:185–194 (1983).

Katayama, M., et al., "Determination of Hydrogen Peroxide by Flow Injection Analysis with Aryl Oxalate–Sulforhodamine 101 Chemiluminescence", *Analytical Letters*, 24(6), pp. 1005–1015 (1991).

Takayasu, S., et al., "Chemiluminescent Enzyme Immunoassay Using β-D-Galactosidase as the Label and the Bis(2,4,5-trichlorophenyl)oxalate–Fluorescent Dye System", *Journal of Immunological Methods*, 83, pp. 317–325 (1985).

Nakashima, K., et al., "High Performance Liquid Chromatography with Chemiluminescence Detection of Methamphetamine and its Related Compounds Using 4-(N, N-Dimethylaminosulphonyl)-7-fluoro-2,1, 3-benzoxadiazole", *Biomedical Chromatography*, vol. 6, pp. 149–154 (1992).

Bador, R., et al., "Erythrosin as energy acceptor in a biphasic chemiluminescent system for glucose oxidase detection", *Analytica Chimica Acta*, 251, pp. 215–222 (1991).

*Primary Examiner*—Lora M. Green
*Attorney, Agent, or Firm*—Rothwell, Figg, Ernst & Kurz

[57] ABSTRACT

A method of detecting substances, if desired in biological fluids, by using detection reactions based on chemiluminescence, wherein a luminophore, preferably having an emission wavelength longer than about 500 nm, is raised from its non-excited state into an excited state by electron transfer due to the detection reaction, and subsequently the radiation emitted by the luminophore when falling back into its non-excited state is measured. The chemiluminescence reaction is based on the oxidative decomposition of optionally substituted oxalates or oxamides, the radiation emitted by the luminophore when falling back into its non-excited state is of longer wavelength than the nonspecific background radiation of the reaction. The luminophore can be accumulated prior to the chemiluminesence reaction. Nonspecific background radiation of the reaction can be quenched.

40 Claims, No Drawings

METHOD OF DETECTING SUBSTANCES BY CHEMILUMINESCENCE

This is a continuation of application Ser. No. 08/096,818, filed Jul. 29, 1993 now abandoned.

FIELD OF THE INVENTION

The present invention relates to a method of detecting substances by means of detection reactions based on chemiluminescence, if desired in the presence of basic catalysts, wherein a luminophore is raised from its non-excited state into an excited state by electron transfer due to the detection reaction, and subsequently the radiation emitted by the luminophore when falling back into its non-excited state is measured.

BACKGROUND OF THE INVENTION

Within the last two decades, numerous techniques for the qualitative and quantitative detection of various substances have been developed. In molecular biology as well as in immunology, a problem has arisen. On one hand, such detection techniques require detection at the lowest concentration ranges, while on the other hand, the use of radioactive markers, as is common, for instance, with various techniques for detecting DNA and RNA, or fragments thereof, is to be avoided. Many of the current detection methods are unable to detect extremely low concentrations (picomole, femtomole and attomole ranges) of substances in biologic samples and thus are unable to produce detectable signals.

Recently, it has been proposed to employ chemiluminescence methods instead of fluorometric, spectrophotometric or radiometric measurements. With such chemiluminescence methods, an energy turnover related to a chemical reaction is made accessible to measurement, wherein, e.g., energy-rich, instable intermediate stages forming in a specific chemical process immediately disintegrate, the energy thereby released being transformed into visible and measurable radiation by so-called luminophores or fluorogens.

British Patent No. 1,461,877 describes a method of assaying a substrate in a body fluid, wherein a specific enzyme catalyzes the reaction of the substrate so as to produce hydrogen peroxide which in turn reacts with a chemiluminescent compound to cause emission of light.

Chemiluminescence reactions may be associated with biochemical reactions by coupling luminophores to a substrate to be cleaved, for instance by an enzyme. This cleavage inactivates the substrate-luminophore complex (the inactive substrate-luminophore complex, in general, is denoted as a fluorogen) and the amount of luminophore released due to the action of the enzyme on the substrate is a measure of the amount of enzyme present in the sample. On account of the catalytic activity inherent in enzymes, a kind of "enzymatic amplification" occurs, which manifests itself by the released amount of luminophore being a multiple of the amount of enzyme present in the sample, while also corresponding to the incubation time as well as to the specific enzyme activity. The term "enzyme" used herein is meant to comprise all substances that exhibit a biological catalyzing effect. Such enzymes may be conjugated with other biological molecules, such as including antigens, antibodies as well as nucleic acid molecules.

In Bronstein et al., "Chemiluminescent Compounds for Diagnostic Tests", Research, Vol. 28, pp. 36–39 (January 1990), a chemiluminescence system has been proposed wherein modified 1,2-dioxetanes are used as fluorophores. Upon hydrolysis, these fluorophores produce anions, which subsequently undergo further decomposition resulting in light emission. Such a direct chemiluminescence derivative contains a "weak" oxygen/oxygen bond which easily breaks, triggering the decomposition of the fluorogen into two products. Both products contain a strong, newly formed carbonyl group. One of these carbonyl groups initially is in an electronically excited state, releasing approximately 420 KJ/mole of energy while returning to its normal ground state. Some of this energy is released in the form of light. In this manner, a strong chemiluminescence signal is produced.

The compounds used by Bronstein et al. exhibit luminescence and are capable of emitting fluorescent and phosphorescent light upon excitation. However, the fluorophores described and used by Bronstein et al. require several different substituents, including a stabilizing moiety consisting of a spiroadamantyl nucleus, an aryl group (from which light is emitted upon fragmentation of the dioxetane) and an enzyme-labile protecting function. The protecting function must be cleaved by the appropriate enzyme to be measured before the chemiluminescence reaction can occur. Thus, the fluorescence exhibiting part of the fluorophore is destroyed during the chemiluminescence reaction. Consequently, the measuring cycle can be passed through only once per mole of fluorophore.

In general, chemiluminescence also may be employed for multiple analyses as is described, e.g., in GB-A-2 233 450, wherein the compounds to be assayed are each "labelled" with luminophores having different emission wavelengths.

In the application of chemiluminescence to analytical problems, the classes of luminol derivatives which play a leading role as luminophores include acridinium derivatives, phenantridinium derivatives, biogenic luciferin-luciferase systems and stable dioxetanes. Conventional luminescence systems usually require basic catalysts or other catalysts as well as the presence of other compounds for boosting, stabilizing or translating the energy released by the system into measurable light emission. For example, GB-A-2 233 451 describes the use of water soluble enhancer substances for stabilizing light-emitting fluorophores in aqueous media, thus increasing the intensity of the emitted light.

The optimization of chemiluminescence reactions by adding further reagents, however, has proved technically difficult in most systems. The simultaneous addition of these reagents produce unacceptably high levels of background radiation in the reactions, thus causing problems in measuring the proper signal. On the other hand, adding too few additives results in diminished signals.

It was suggested by Campbell et al., Biochem. J., Vol. 216, pp. 185–194 (1983), to use for a detection method the energy transfer occurring between a chemiluminescence donor coupled to an antigen (Ag-L) and a fluorescence acceptor coupled to an antibody (Ab-F), the chemiluminescence-donor-coupled antigen (Ag-L) competing with the unlabelled antigen (Ag) to be measured, in binding with the fluorescence-acceptor-coupled antibody (Ab-F). In doing so, either a complex (L-AgAb-F) having an emitted wavelength (based on the possible energy transfer) that differs from that of the (Ag-L) complex, or a (AgAb-F) complex (in which no energy transfer is feasible) is formed. Subsequently, the radiation intensity is measured at two wavelengths, i.e., at the emitted wavelength of the (Ag-L) complex, and at the emitted wavelength of the (L-AgAb-F) complex, while filtering off the respective other signal, which itself also is concentration-specific for better signal separation.

In the above technique, the amount of unlabelled antigen (to be detected) is detectable from the decrease of the intensity ratios of the two signals. This difference is, however, only minimal in the case of slight amounts that are to be detected. Since such a "homogenous immunoassay" is a competitive system, it also involves, in addition to the above-mentioned problems faced in detecting slight, even the slightest, amounts of a substance, considerable practical problems with measuring the amounts, for instance, of antigen coupled to the chemiluminescence donor (Ag-L). These amounts must approximately correspond to the amounts of non-labelled antigen to be detected. The measuring device used, such as a chemiluminometer, also must be equipped with appropriate detectors at the two wavelengths. The detection limit of this system lies at approximately $10^{-16}$ mol/100 ul.

A method of quantifying oxalate of the general formula $R^1R^2(COO)_2$ is disclosed in DD-A 280,824. In this method, oxalic acid, or the oxalate-containing sample solution, is transformed into monoperoxyoxalic acid by a suitable oxidizing agent. The decomposition of the monoperoxyoxalic acid in the presence of an activator produces an emission of photons capable of being registered by a chemiluminescence measuring device.

The peroxyoxalate chemiluminescence reaction, like almost all chemiluminescence reactions based on the oxidative decomposition of optionally substituted oxalates or oxamides, has been limited to use in aprotic media. Hence, there has been a prejudice against using this chemiluminescence reaction as a detection reaction for bioassays. In particular, the peroxyoxalate system has been unusable in immunoassays or other bioassays on account of its low solubility and insufficient resistance to solvolysis in protic media; e.g., aqueous systems. These disadvantages result in light emission of considerably lessened intensity upon decomposition of the selected chemiluminescent compound. Accordingly, there exists a need for a method of using the peroxyoxalate detection system in protic media, especially in aqueous media, that enables more sensitive detection of substances in immunoassays as well as other bioassays.

SUMMARY OF THE INVENTION

The present invention is directed to a method that satisfies this need. The method enables the detection of substances in bioassays by means of detection reactions based on chemiluminescence. In this method, a luminophore, preferably having an emission wavelength longer than about 500 nm, is used in a chemiluminescence reaction. A preferred chemiluminescence reaction is the peroxyoxalate reaction, based on the oxidative decomposition of optionally substituted oxalates or oxamides. As the excited luminophore returns to its non-excited state, it emits radiation having a longer wavelength than the nonspecific background radiation of the reaction. The nonspecific background radiation of the reaction can be substantially quenched by means of a suitable wavelength selection unit and/or the luminophore can be purposefully accumulated via an additional chemical or enzymatic reaction prior to carrying out the chemiluminescence reaction.

In one preferred embodiment, the method of the present invention offers a highly sensitive means for detecting human immunodeficiency virus (HIV).

These and other features, aspects and advantages of the present invention will become better understood with reference to the following description and appended claims.

DETAILED DESCRIPTION OF THE INVENTION

A method is provided which enables the use of the peroxyoxalate detection system in protic media. The method permits the use of direct luminophore labelling of a substance to be detected, in particular in chemiluminescence amplified enzyme immunoassays. The difficulties faced in connection with the incompatibility of the peroxyoxalate reaction with protic media, on account of insufficient resistance to solvolysis and low solubility, have been overcome by the use of a new solvent system, preferably consisting of about 50 percent water. Specifically, an enormous improvement of the detection limit for the luminophore and, consequently, for the substance to be detected can be achieved when using the peroxyoxalate reaction as a detection reaction in an enzyme immunoassay. An appropriate luminophore is chosen which emits radiation at a longer wavelength than the background radiation of the reaction employed, preferably longer than about 500 nm.

The practical application of the peroxyoxalate chemiluminescence system has primarily been limited to the detection of species in high pressure liquid chromatography (HPLC) eluants. As stated above, the system has not been useful in immunologic techniques because of the low solubility of reactants and insufficient resistance to solvolysis in protic media. When used as an HPLC detector, low concentrations of luminophores can be detected with such peroxyoxalate systems based on chemically induced electron exchange luminescence (CIEEL). The reaction is useful in this system because, in the absence of a luminophore, the oxidation reaction, emits orders of magnitude less light than with the addition of a luminophore. The detection limit for luminophore concentrations can be enhanced by orders of magnitude when a special luminophore is used, preferably in combination with a suitable wavelength selection unit, in accordance with the present invention.

The signal to be measured also can be amplified by means of chemical or enzymatic reaction(s), over the nonspecific background radiation of the chemiluminescence reaction used, or alternatively by accumulating the non-excited luminophore prior to adding the optionally substituted oxalate ester required for generating energy-rich intermediate stages of the peroxyoxalate system. Considerable "chemical amplification" of the signal to be detected thereby is attained, and the use of a wavelength selection unit for quenching the nonspecific background radiation can for some applications be obviated.

In accordance with the invention, the use of a new solvent system for the first time allows the use in bioassays of chemiluminescence reactions, preferably the peroxyoxalate system, based on the oxidative decomposition of optionally substituted oxalates or oxamides. In particular, the detection reactions can occur as part of a bioassay system in which the biochemical reaction in aqueous solution occurs first, while the chemiluminescence reaction is effected afterwards by adding the necessary reagents in a suitable aprotic solvent or other known solvent system, such as acetonitrile. It is thus possible to use practically unlimited high concentrations of water in a particular bioassay, a water concentration of about 50 percent being particularly preferred.

The peroxyoxalate reaction is a highly potent chemiluminescence system offering a particularly high quantum yield (up to 0.4 Einsteins/mol). In addition to the drawbacks pointed out above in the background section, this system, so far, has not been applicable to bioassays, i.e., to detecting the slightest amounts, because of its strong background radiation in a range of between 350 to 540 nm.

It is favorable to use in the peroxyoxalate chemiluminescence reaction a redox-sensitive luminophore, which emits radiation when falling back into its non-excited state at a wavelength longer than approximately 500 nm. It also is favorable that a wavelength selection unit be used that substantially quenches the background radiation between about 350 and about 540 nm. Wavelength selection units suitable for the method according to the invention include cutoff filters, interferance filters, grids or prisms.

The use of the peroxyoxalate reaction offers the advantage that the luminophore used does not get destroyed, thus being able to run through the excitation cycle more than once. A quantum yield amounting to more than 2 Einsteins (based on the luminophore) thus appears to be feasible. By using a luminophore which emits radiation when falling back into the non-excited state at a wavelength longer than about 500 nm, while simultaneously quenching the background radiation at about 350 to 540 nm by a suitable wavelength selection unit, the background radiation is considerably reduced or even quenched at the detection wavelength, and the detection limit for the luminophore used is thus greatly enhanced.

Theoretically, all compounds having an emission spectrum of wavelengths longer than about 500 nm may be employed as luminophores in the present invention. The use of resorufinate, tetraphenyl porphyrin, rhodamine 123, chlorophyll and/or (Z,Z)-16,17-difluoroboryl-13-ethyl-2,3,7,8,12,14-hexamethyl-1,17-dihydro-15H-tripyrrin-1-one are particularly preferred.

It is preferred that the redox-sensitive luminophore used in the method according to the present invention is one that is released from a suitable substrate under the direct influence of a substance to be detected. It is thus possible to use the highly sensitive detection method according to the present invention for detecting any desired substance, the only prerequisite being the choice of a suitable substrate. This substrate is then coupled to the luminophore, thus inactivating the same. During the detection reaction under the influence of the substance to be detected, this inactivation of the luminophore is reversed, thus rendering the luminophore accessible to activation by electron transfer.

It is particularly advantageous if a fluorogen consisting of a substrate and a luminophore is used, the luminophore being activated or cleaved from the substrate under the direct influence of an amount of enzyme to be detected. Thus, for instance, at a turnover rate of about 1000/s for the enzyme after an incubation time of 30 minutes, a number of about $1.8 \times 10^6$ mol luminophore per mole of enzyme will be present, thus considerably enhancing the signal. After this incubation time, the peroxyoxalate reaction is then started and the signal produced is measured. In doing so, it is particularly advantageous that no measurements be carried out during the incubation time, thus allowing considerable savings in time, in particular, when carrying out serial assays.

The enzyme used for setting free or activating the luminophore may be bound directly or indirectly to an antibody, an antigen or a nucleic acid probe. It should be mentioned that the term "indirectly bound" refers to any bond between an enzyme and an antibody, antigen or nucleic acid probe, in which the respective substances are connected not directly, but via inorganic or organic spacers as are known, for instance, from affinity chromatography.

A variety of enzyme-substrate combinations are known and may be used in the method of this invention. Enzymes for setting free or activating the luminophore by acting on a luminophore/substrate complex, include, for example, alkaline phophatase, horseradish peroxidase and β-galactosidase.

According to another preferred embodiment of the present invention, the luminophore used can be activated or released from a suitable substrate under the indirect influence of a substance to be detected. The use of the method according to the invention in so called "cascade-like" assaying techniques is possible. These kinds of reactions are known, for instance, from the blood coagulation cascade. By this technique, an additional chemical and/or enzymatic amplification of the signal attainable by direct reaction is feasible at any individual stage of the cascade.

In a more preferred embodiment of the present invention, the indirect influence of an amount of antigen or antibody to be detected on a respective antibody or antigen, coupled with an enzyme which sets free the luminophore, is effected via one or several additional antigen-antibody reactions. In doing so, not only amplification of the attainable signal is achieved, but also a particularly specific quantitive detection is feasible. Thus, it is possible to detect an HIV-antigen by using an anti-HIV antibody from rabbit and an anti-rabbit antibody from goat coupled with an enzyme, the enzyme subsequently setting free the luminophore from a luminophore-substrate complex.

In an alternative favorable embodiment of the method of this invention, one or more reactants may be provided which contain a binding site for another component which may in turn be coupled to an enzyme. A system of this type would, for instance, be a system comprising biotin coupled to the antibody and an avidin or streptavidin-enzyme complex or, in general, any known combination of coupling partners, the enzyme used for setting free the luminophore being bound to one of the partners.

It also should be mentioned that an inversed detection method may be used, wherein the decrease in the emitted radiation relative to a blind sample being measured by the spatial presence of a quencher.

The invention now being generally described, the same will be better understood by reference to the following examples which are provided for purposes of illustration only and are not intended to be limiting of the invention.

EXAMPLE 1

Calculation of Quantum Efficiency

10 µl of a solution of 125 mg urea peroxide in 4 ml water, 10 µl of (Z,Z)-16,17-difluoroboryl-13-ethyl-2,3,7,8,12,14-hexamethyl-1,17-dihydro-15H-tripyrrin-1-one (GR 132) in ethylacetate, and 200 µl of a 1 mM-solution of bis(2,4-dinitrophenyl) oxalate (DNPO) in ethylacetate were applied into a glass tubing. Light impulses that were produced were immediately integrated over 5 minutes on a Mamamatsu MTP-Reader. A blank also was tested, to which 10 µl of pure ethylacetate was pipetted instead of the 10 µl of GR 132 solution.

GR 132 was obtained from Doz. Grubruayr, Institute for Organic Chemistry, University in Linz. Blistered urea peroxide was obtained from an HIV antibody assay of Organon Teknika. DNPO was obtained from Lambda Probes, Graz. Ethylacetate and water of spectrograde purity were obtained from Merck, Darmstad. The luminometrical measurements were performed on a Mamamatsu MTP-Reader that was equipped with a Moya FL Red-Filter.

To detect sensitivity and quantum efficiency, a dilution series of GR 132 in ethylacetate was performed. The dilution series was done until a concentration of $2.3 \times 10^8$ molecules per tubing was reached. Due to losses because of geometry, optics and the detection unit, 14,000 impulses were predicted. At a signal/noise ratio of 4, 30,000 impulses were measured after deducting the impulses emitted from the blank. This resulted in a quantum efficiency of more than 2, related to the selected luminophore, GR 132.

EXAMPLE 2

Improvement of Sensitivity using a Filter in the Peroxyoxalate Reaction

Resorufin sodium salt was diluted in imadazole buffer (7 mg imidazole/10 ml $H_2O$). 10 µl of a urea peroxide solution in water (125 mg/10 ml) and 200 ml of a solution of Bis(2,4,6-trichlorophenyl) oxalate (TCPO) in acetonitrile (1 mM) were pipetted into 100 µl of the above dilution in a Berthold tubing. The luminometer was closed and the detection in the 10S integral mode was started. The optical reaction density was read in a microliter plate on an Anthos ht 111 photometer at 570 nm having a reference wavelength of 620 nm.

TCPO was synthesized at the Institute for Organic Chemistry, University in Linz, and was crystallized twice from ethylacetate. Imidazole from Merck was crystallized from ether. Water was obtained of Uvasol quality and acetonitrile was obtained from Promochem Chrom AR. Blistered urea peroxide was taken from an HIV antibody assay from Organon Teknika. Sodium resorufinate was obtained from Lambda Probes, Graz. Luminometric measurements were taken on a Berthold Biolumat LB 9500T luminometer (to which Berthold tubing properly fits), which was equipped with an OG 590 nm filter from Schott (1 mm) between the tubing holder and photomultiplier.

The measured values were as follows:

TABLE I

| | | Without Filter | | With Filter | |
|---|---|---|---|---|---|
| Concentration | Extinction | Counts | S/N* | Counts | S/N |
| $1.40 \times 10^{-6}$ | 0.093 | Overflow | | Overflow | |
| $3.50 \times 10^{-7}$ | 0.021 | Overflow | | Overflow | |
| $8.74 \times 10^{-8}$ | 0.004 | Overflow | | 420,786 | 253 |
| $2.19 \times 10^{-8}$ | −0.001 | 478,395 | 2.15 | 103,309 | 62.1 |
| $5.46 \times 10^{-9}$ | 0.000 | 301,335 | 1.16 | 26,864 | 16.1 |
| $1.37 \times 10^{-9}$ | −0.003 | 284,350 | 1.28 | 7,636 | 4.59 |
| $3.42 \times 10^{-10}$ | −0.001 | 237,460 | 1.07 | 3,016 | 1.81 |
| $8.54 \times 10^{-11}$ | −0.002 | 223,395 | 1.006 | 2,146 | 1.29 |
| $2.13 \times 10^{-11}$ | −0.002 | 222,090 | 1.0001 | 1,872 | 1.13 |
| $5.34 \times 10^{-12}$ | −0.001 | 220,700 | 0.993 | 7,710 | 1.03 |

* Signal/Noise

One can see from the above data that using a filter for quenching the nonspecific background radiation improves the sensitivity of the reaction system by a factor of about 100.

EXAMPLE 3

Detection of β-galactosidase

A dilution series of avidin β-galactosidase in HEPES/BSA (20 mM Hepes, 0.5M NaCl, pH 7.5 with 1.0 mg/ml BSA) was done. 10 µl of this dilution series was placed onto a microliterplate from Organon Tekhika, and 100 µl of a substrate buffer ($1\times10^{-4}$M resorufin-β-D-galactopyranoside, 0.1M NaCl, 2 mM $MgCl_2$, 5 mM imidazole) was added and incubated for 90 minutes at 37° C. The optical density then was measured, whereafter, 100 µl of the substrate buffer was transferred to a tube. 10 µl of $H_2O_2$ (1M Uvasol $H_2O$) then was added, and thereafter was transferred to a luminometer. 100 µl of a solution of TCPO in acetonitrile next was added (1 mM), whereupon the luminometer was manually started and recorded counts in the 10S integral mode. A molar weight of β-galactosidase of 500,000 was assumed for the calculation.

Avidin β-galactosidase was obtained from Pierce and resorufin-β-D-galactopyranoside was obtained from Lambda Probes, Graz. $MgCl_2.6H_2O$ and NaCl were obtained from Merck, while HEPES/BSA-buffer was obtained from Codon, Vienna. Resorufin-β-D-galactopyranoside was dissolved in chloroform/methanol (4:1), on silica 60 with chloroform/methanol/water (260:70:10) as elements separated from impurities and dried in a high vacuum at room temperature. The light reddish product obtained was crystallized twice from Uvasol water at 60° C., washed with Uvasol water and dried with spectrograde acetonitrile.

The measured values were as follows:

TABLE II

| Molecules | Extinction | Counts | S/N |
|---|---|---|---|
| $5.8 \times 10^8$ | 0.467 | Overflow | |
| $1.5 \times 10^8$ | 0.159 | Overflow | |
| $3.6 \times 10^7$ | 0.051 | Overflow | |
| $9.1 \times 10^6$ | 0.016 | Overflow | |
| $2.3 \times 10^6$ | 0.006 | Overflow | |
| 568,432 | 0.004 | Overflow | |
| 142,108 | 0.000 | 480,304 | 2.61 |
| 35,527 | −0.001 | 335,438 | 1.82 |
| 8,882 | −0.001 | 283,060 | 1.54 |
| 2,220 | −0.001 | 243,697 | 1.32 |
| 555 | −0.003 | 199,791 | 1.09 |
| 139 | −0.001 | 183,964 | 1.00 |

The described procedure has a very low coefficient of variation. (The use of an automatic pipetting device would further decrease the coefficient of variation.). As evident from the above data, less than 1000 molecules in 100 ml can be detected in less than 2 hours.

EXAMPLE 4

Detection of Horseradish-Peroxidase (HRP)

A dilution series (1:10) of anti-human IgG peroxidase-conjugate in conjugate-diluent was done in an Organon Teknika dilution microtiter plate. For a photometric detection, 10 µl of one dilution was pipetted into 100 µl of a substrate reagent (tetramethylbenzidine reagent/peroxide reagent=1:10). For a luminometric detection, 10 µl of one dilution was pipetted into 100 µl of a substrate reagent (10 µl of a $10^{-3}$M solution of dihydrorhodamine 123 in acetonitrile and 30 µl of peroxide reagent). Both samples were incubated for 15 minutes, whereafter the photometric sample was read at 620 nm with an Anthos photometer. 100 µl of a 0.1 mM solution of TCPO in acetonitrile was added to 100 µl of the luminometric sample in a Berthold tube and the luminometer was manually started and counts were recorded in the 10S integral mode.

Anti-human IgG-peroxidase conjugate, conjugate-diluent, tetramethylbenzidine reagent and peroxide reagent were taken from a Detect HIV test kit from Coulter. Dihydrorhodamine 123 was obtained from Lambda Probes Graz. The luminescence was measured on a Berthold LB9500T luminometer equipped with an OG530 nm filter (3 mm) between the tube holder and photomultiplier.

The measured values were as follows:

TABLE III

| Arbitrary Concentration | Extinction | Counts | S/N |
|---|---|---|---|
| 10,000 | 0.320 | 837,889 | 200 |
| 1,000 | 0.038 | 23,363 | 5.57 |
| 100 | 0.039 | 5,711 | 1.36 |
| 10 | 0.041 | 4,011 | 0.96 |
| 1 | 0.043 | 4,374 | 1.04 |

The above data show that the detection limit of HRP improved by a factor of 100.

EXAMPLE 5

Detection of Alkaline Phosphatase

A dilution series was done of streptavidin alkaline phosphatase-conjugate in HEPES/BSA (20 mM Hepes, 0.5M NaCl, pH 7.5 with 1.0 mg/ml BSA). 100 µl of a substrate buffer ($1 \times 10^{-5}$M resorufinatephosphate-pyridinium salt, 0.1M NaCl, 1 mM $MgCl_2$, 0.01M carbonate buffer, pH 9.6) were added to 10 µl of the above dilution and incubated at 37° for 90 minutes. After measuring the optical density (570/620 nm), 100 µl was transferred to a tube, to which 10 µl $H_2O_2$ (1M Uvasol $H_2O$) was added. The reaction solution then was transferred to the luminometer, to which 100 µl of a solution of TCPO in acetonitrile were added (1 mM). The luminometer was manually started and counts were recorded in the 10S integral mode. For the calculation, a molar weight of 75,000 for alkaline phosphatase was assumed.

Equipment was obtained as in Example 2. Streptavidin alkaline phosphatase-conjugate was obtained from Pierce, while resorufinate phosphate - pyridinium salt was obtained from Lambda Probes, Graz. The carbonate buffer (0.01M, pH 9.6, 1 mM $MgCl_2$) was obtained from Codon, Vienna. All other reagents were obtained as already noted in the above Examples 1–4. An OG 590 nm filter (1 mm) was used with the luminometer.

The measured values were as follows:

TABLE IV

| Molecules | Extinction | Count | S/N |
|---|---|---|---|
| $1.2 \times 10^{10}$ | 0.182 | Overflow | |
| $3 \times 10^9$ | 0.179 | Overflow | |
| $7.5 \times 10^8$ | 0.129 | Overflow | |
| $1.9 \times 10^8$ | 0.027 | Overflow | |
| $4.7 \times 10^7$ | 0.011 | 284,891 | 6.22 |
| $1.2 \times 10^7$ | 0.009 | 63,629 | 1.39 |
| 2,925,146 | 0.008 | 46,100 | 1.006 |
| 731,286 | 0.008 | 45,392 | 0.991 |
| 182,822 | 0.008 | 48,447 | 1.057 |
| 45,705 | 0.008 | 43,314 | 0.945 |

The above data indicates that the sensitivity achieved by using the luminometer detection system can be improved by a factor of 10 as compared to using the above reagent system with a photometric detection system.

EXAMPLE 6

Detection of HIV-1 p24 Antigen

An HIV-1 p24 antigen Elisa assay was done according to the protocol provided with Retro-Tek HIV-1 p24 antigen Elisa assay kit (Cellular Products, Buffalo). A solution of β-galactosidase diluted by a factor of 1:10,000 in HEPES/BSA buffer (20 mM HEPES, 0.5M NaCl, pH 7.5, with 1.0 mg/ml BSA) was used instead of a streptavidin-peroxidase - working solution. 100 µl of a substrate buffer ($1 \times 10^{-4}$M resorufin-β-D-galactopyranoside, 0.M NaCl, 2 mM $MgCl_2$, 5 mM imidazole) was used for the luminometric detection method. The buffer was incubated at 37° C. for 90 minutes. 100 µl of the buffer were transferred to a tube, along with 10 µl $H_2O_2$ (1M Uvasol $H_2O$). The reaction solution next was transferred to the luminometer, to which 100 µl of a solution of TCPO in acetonitrile were added (1 mM). The luminometer was manually started and counts were recorded in the 10S integral mode. The washing buffer provided in the assay kit also was used.

Avidin-β-galactosidase, was obtained from Pierce, while resorufin-β-D-galactopyranoside was obtained from Lambda Probes, Graz. $MgCl_2.6H_2O$ and NaCl were obtained from Merck, while HEPES/BSA buffer was obtained from Codon, Vienna.

The measured values were as follows:

TABLE V

| PP/ML | Extinction | Counts | S/N |
|---|---|---|---|
| 125 | 1.652 | 351,040 | 6.46 |
| 31.25 | 0.430 | 148,277 | 2.73 |
| 7.81 | 0.146 | 79,169 | 1.45 |
| 1.95 | 0.058 | 64,016 | 1.18 |
| 0.49 | 0.038 | 57,227 | 1.05 |
| 0.12 | 0.033 | 54,304 | 1.00 |

It is evident from the above data that the luminometric detection system produces the same results under suboptimal conditions as with a photometric detection system. The data further show that the detection system can be used with Elisa-based systems.

COMPARATIVE EXAMPLE

Detection of Pd-Coproporphyrin

Pd-Coproporphyrin was dissolved in acetone/imidazole buffer ($10^{-2}$M, pH 7), whereafter a dilution series in imidazole buffer was made. To 100 µl of the buffer, 10 µl of urea peroxide solution (125 mg/10 ml $H_2O$) and 200 µl of acetonitrile (1 mM TCPO) were added. The luminometer was immediately started and counts in the 10S integral mode were detected.

Pd-Coproporphyrin was obtained from Lambda Probes, Graz. The remaining reagents were obtained, as already identified in Examples 1 and 2. The luminometer was equipped with an OG 590 nm filter obtained from Schott (1 mm).

The measured values were as follows:

TABLE VI

| Concentration | Counts | S/N |
|---|---|---|
| $8.40 \times 10^{-7}$ | Overflow | |
| $2.10 \times 10^{-7}$ | Overflow | |
| $5.25 \times 10^{-8}$ | Overflow | |
| $1.31 \times 10^{-8}$ | 677 | 4.12 |
| $3.28 \times 10^{-9}$ | 285 | 1.73 |
| $8.20 \times 10^{-10}$ | 191 | 1.07 |
| $2.05 \times 10^{-10}$ | 171 | 1.04 |
| $5.13 \times 10^{-11}$ | 168 | 1.02 |
| $1.28 \times 10^{-11}$ | 160 | 0.98 |

One can see from the above results that water soluble Pd-Coproporphyrin can be measured to low concentrations of $8 \times 10^{-10}$ mol/l. This result cannot compete, however, with GR 132 ($3.9 \times 10^{-11}$ mol/l) or sodium resorufinate ($2.13 \times 10^{-11}$ mol/l).

What is claimed is:

1. A method of detecting a substance by chemiluminescence in an aqueous solvent system wherein the solvent system further comprises a solvent in addition to water which is compatible with the peroxyoxalate chemiluminescent reaction, wherein a luminophore is raised from its non-excited state into an excited state by electron transfer and subsequently the radiation emitted by the luminophore when falling back into its non-excited state is measured, comprising the steps of:

(a) employing a redox-sensitive luminophore in said aqueous solvent system wherein the luminophore is released from a substrate by an enzyme, wherein the enzyme is the substance being detected or is bound to a binding partner of the substance being detected;

(b) adding an oxidant and an optionally substituted oxalate or an oxamide to the reaction wherein in a chemiluminescent reaction said luminophore is raised from a non-excited state into an excited state by electron transfer due to the oxidative decomposition of the optionally substituted oxalate or oxamide, said luminophore thereby emitting radiation when falling back into its non-excited state, wherein said emitted radiation has a longer wavelength than nonspecific background radiation;

(c) quenching the nonspecific background radiation of said chemiluminescent reaction at about 350 nm to 540 nm with a suitable wavelength selection unit; and (d) measuring the amount of radiation emitted by the luminophore, thereby detecting as low as about $10^{-11}$ mol/l of the substance being detected.

2. A method according to claim 1, wherein the enzyme is directly bound to a binding partner of the substance being detected.

3. The method of claim 1, wherein the enzyme is indirectly bound to a binding partner of the substance being detected.

4. A method according to claim 1, wherein the chemiluminescence reaction is a peroxyoxalate reaction.

5. A method according to claim 4, wherein the luminophore emits radiation when falling back into its non-excited state having a wavelength longer than about 500 nm.

6. A method according to claim 5, wherein the luminophore is selected from the group consisting of resorufinate, tetraphenyl porphyrin, rhodamine 123, chlorophyll and (Z-Z)-16,17-difluoroboryl-13-ethyl-2,3,7,8,12,14-hexamethyl-1,17-dihydro-15H-tripyrrin-1-one.

7. A method according to claim 6, wherein the luminophore is resorufinate.

8. A method according to claim 6, wherein the luminophore is rhodamine 123.

9. A method according to claims 1 or 6, wherein the substance to be detected is in a biological fluid.

10. A method according to claim 9, wherein the biological fluid contains about 50 percent water.

11. A method according to claim 9, wherein the substance to be detected is an enzyme.

12. A method according to claim 11, wherein the enzyme is bound to an antibody, an antigen, or a nucleic acid probe.

13. A method according to claim 12, wherein the enzyme is bound to an antibody.

14. A method according to claim 13, wherein the antibody is an anti-HIV antibody.

15. A method according to claim 12, wherein the enzyme is bound to an antigen.

16. A method according to claim 15, wherein the antigen is HIV antigen.

17. A method according to claim 13, wherein the enzyme is indirectly bound to an antibody.

18. A method according to claim 17, wherein the enzyme is indirectly bound to the antibody by avidin or streptavidin.

19. A method according to claim 17, wherein the enzyme is indirectly bound to an anti-HIV antibody.

20. A method according to claim 11, wherein the enzyme is selected from the group consisting of alkaline phosphatase, horseradish peroxidase, and β-galactosidase.

21. A method of detecting a substance by chemiluminescence in an aqueous solvent system wherein the solvent system further comprises a solvent in addition to water which is compatible with the peroxyoxalate chemiluminescent reaction, wherein a luminophore is raised from its non-excited state into an excited state by electron transfer and subsequently the radiation emitted by the luminophore when falling back into its non-excited state is measured, comprising the steps of:

(a) accumulating a redox-sensitive luminophore, wherein the luminophore is released from a substrate by an enzyme, wherein the enzyme is the substance being detected or is bound to a binding partner of the substance being detected;

(b) adding an oxidant and an optionally substituted oxalate or an oxamide to the reaction wherein in a chemiluminescent reaction said luminophore is raised from a non-excited state into an excited state by electron transfer due to the oxidative decomposition of the optionally substituted oxalate or oxamide, said luminophore thereby emitting radiation when falling back into its non-excited state, wherein said emitted radiation has a longer wavelength than nonspecific background radiation;

(c) quenching the nonspecific background radiation of said chemiluminescent reaction at about 350 nm to 540 nm with a suitable wavelength selection unit; and (d) measuring the amount of radiation emitted by the luminophore, thereby detecting as low as about $10^{-11}$ mol/l of the substance being detected.

22. The method of claim 21, wherein the enzyme is directly bound to a binding partner of the substance being detected.

23. The method of claim 21, wherein the enzyme is indirectly bound to a binding partner of the substance being detected.

24. A method according to claim 21, wherein the chemiluminescence reaction is a peroxyoxalate reaction.

25. A method according to claim 24, wherein the luminophore emits radiation when falling back into its non-excited state having a wavelength longer than about 500 nm.

26. A method according to claim 25, wherein the luminophore is selected from the group consisting of resorufinate, tetraphenyl porphyrin, rhodamine 123, chlorophyll and (Z-Z)-16,17-difluoroboryl-13-ethyl-2,3,7,8,12,14-hexamethyl-1,17-dihydro-15H-tripyrrin-1-one.

27. A method according to claim 26, wherein the luminophore is resorufinate.

28. A method according to claim 26, wherein the luminophore is rhodamine 123.

29. A method according to claims 21 or 36, wherein the substance to be detected is in a biological fluid.

30. A method according to claim 29, wherein the biological fluid contains about 50 percent water.

31. A method according to claim 29, wherein the substance to be detected is an enzyme.

32. A method according to claim 31, wherein the enzyme is bound to an antibody, an antigen, or a nucleic acid probe.

33. A method according to claim 32, wherein the enzyme is bound to an antibody.

34. A method according to claim 33, wherein the antibody is an anti-HIV antibody.

35. A method according to claim 32, wherein the enzyme is bound to an antigen.

36. A method according to claim 35, wherein the antigen is HIV antigen.

37. A method according to claim 33, wherein the enzyme is directly bound to an antibody.

38. A method according to claim 37, wherein the enzyme is indirectly bound to the antibody by avidin or streptavidin.

39. A method according to claim 37, wherein the enzyme is indirectly bound to an anti-HIV antibody.

40. A method according to claim 31, wherein the enzyme is selected from the group consisting of alkaline phosphatase, horseradish peroxidase, and β-galactosidase.

* * * * *

UNITED STATES PATENT AND TRADEMARK OFFICE
CERTIFICATE OF CORRECTION

PATENT NO. : 5,736,320
DATED : April 7, 1998
INVENTOR(S) : Thomas Schlederer et al.

It is certified that error appears in the above-indentified patent and that said Letters Patent is hereby corrected as shown below:

Col. 13, line 10, "directly" should be -- indirectly --.

Signed and Sealed this

Sixteenth Day of January, 2001

Attest:

Attesting Officer

Q. TODD DICKINSON
Commissioner of Patents and Trademarks